(12) United States Patent  (10) Patent No.: US 7,131,860 B2
Sartor et al.  (45) Date of Patent: Nov. 7, 2006

(54) CONNECTOR SYSTEMS FOR ELECTROSURGICAL GENERATOR

(75) Inventors: Joe Don Sartor, Longmont, CO (US); Mark Joseph Huseman, Broomfield, CO (US)

(73) Assignee: Sherwood Services AG, Schaffhausen (CH)

( * ) Notice: Subject to any disclaimer, the term of this patent is extended or adjusted under 35 U.S.C. 154(b) by 369 days.

(21) Appl. No.: 10/718,114

(22) Filed: Nov. 20, 2003

(65) Prior Publication Data

US 2005/0113818 A1  May 26, 2005

(51) Int. Cl.
*H01R 3/00* (2006.01)
(52) U.S. Cl. .......................................... 439/489; 439/42
(58) Field of Classification Search ................ 439/489, 439/909, 912, 218, 219, 692, 651, 650; 606/42, 606/41, 45, 50
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |

(Continued)

FOREIGN PATENT DOCUMENTS

DE  179607  3/1905

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

(Continued)

*Primary Examiner*—Alexander Gilman

(57) ABSTRACT

A connector system for coupling electrosurgical instruments to electrosurgical generators is provided. The connector system includes a plug portion connectable to an electrosurgical instrument, the plug portion of the electrosurgical instrument having a shape specific to a particular manufacturer; and a plug receptacle portion supported on the electrosurgical generator; the plug receptacle portion being shaped to receive the plug portion of the electrosurgical instrument of the particular manufacturer and the plug portion of the electrosurgical instrument of any other manufacturer.

2 Claims, 10 Drawing Sheets

U.S. PATENT DOCUMENTS

| | | |
|---|---|---|
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,437,464 A | 3/1984 | Crow |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Paterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,880,719 A | 11/1989 | Murofushi et al. |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A | 10/1990 | Carder |
| 4,961,435 A | 10/1990 | Kitagawa et al. |
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,015,227 A | 5/1991 | Broadwin et al. |
| 5,019,176 A | 5/1991 | Brandhorst, Jr. |
| 5,029,588 A | 7/1991 | Yock et al. |

| | | | | | |
|---|---|---|---|---|---|
| 5,087,257 A | 2/1992 | Farin | 5,490,850 A | 2/1996 | Ellman et al. |
| 5,088,997 A | 2/1992 | Delahuerga et al. | 5,496,312 A | 3/1996 | Klicek |
| 5,103,804 A | 4/1992 | Abele et al. | 5,496,313 A | 3/1996 | Gentelia et al. |
| 5,108,389 A | 4/1992 | Cosmescu | 5,500,012 A | 3/1996 | Brucker et al. |
| 5,108,391 A | 4/1992 | Flachenecker | 5,500,616 A | 3/1996 | Ochi |
| 5,122,137 A | 6/1992 | Lennox | 5,514,129 A | 5/1996 | Smith |
| 5,133,711 A | 7/1992 | Hagen | 5,520,684 A | 5/1996 | Imran |
| 5,151,102 A | 9/1992 | Kamiyama et al. | 5,531,774 A | 7/1996 | Schulman et al. |
| 5,152,762 A | 10/1992 | McElhenney | 5,534,018 A | 7/1996 | Wahlstrand et al. |
| 5,157,603 A | 10/1992 | Scheller et al. | 5,536,267 A | 7/1996 | Edwards et al. |
| 5,160,334 A | 11/1992 | Billings et al. | 5,540,681 A | 7/1996 | Strul et al. |
| 5,162,217 A | 11/1992 | Hartman | 5,540,683 A | 7/1996 | Ichikawa |
| 5,167,658 A | 12/1992 | Ensslin | 5,540,684 A | 7/1996 | Hassler, Jr. |
| 5,190,517 A | 3/1993 | Zieve et al. | 5,540,724 A | 7/1996 | Cox |
| 5,196,008 A | 3/1993 | Kuenecke | 5,556,396 A | 9/1996 | Cohen et al. |
| 5,196,009 A | 3/1993 | Kirwan, Jr. | 5,558,671 A | 9/1996 | Yates |
| 5,201,900 A | 4/1993 | Nardella | 5,563,402 A * | 10/1996 | Reddersen et al. ......... 235/436 |
| 5,207,691 A | 5/1993 | Nardella | 5,569,242 A | 10/1996 | Lax et al. |
| 5,230,623 A | 7/1993 | Guthrie et al. | 5,571,147 A | 11/1996 | Sluijter et al. |
| 5,233,515 A | 8/1993 | Cosman | 5,573,533 A | 11/1996 | Strul |
| 5,244,462 A | 9/1993 | Delahuerga et al. | 5,588,432 A | 12/1996 | Crowley |
| 5,267,994 A | 12/1993 | Gentelia et al. | 5,594,636 A | 1/1997 | Schauder |
| 5,267,997 A | 12/1993 | Farin | 5,596,466 A | 1/1997 | Ochi |
| 5,281,213 A | 1/1994 | Milder et al. | 5,599,344 A | 2/1997 | Paterson |
| 5,300,068 A | 4/1994 | Rosar et al. | 5,599,345 A | 2/1997 | Edwards et al. |
| 5,300,070 A | 4/1994 | Gentelia | 5,605,150 A | 2/1997 | Radons et al. |
| 5,318,563 A | 6/1994 | Malis et al. | 5,613,966 A | 3/1997 | Makower et al. |
| 5,323,778 A | 6/1994 | Kandarpa et al. | 5,613,996 A | 3/1997 | Lindsay |
| 5,324,283 A | 6/1994 | Heckele | 5,625,370 A | 4/1997 | D'Hont |
| 5,330,518 A | 7/1994 | Neilson et al. | 5,626,575 A | 5/1997 | Crenner |
| 5,334,193 A | 8/1994 | Nardella | 5,628,745 A | 5/1997 | Bek |
| 5,341,807 A | 8/1994 | Nardella | 5,643,330 A | 7/1997 | Holsheimer et al. |
| 5,342,356 A | 8/1994 | Ellman et al. | 5,647,869 A | 7/1997 | Goble et al. |
| 5,342,357 A | 8/1994 | Nardella | 5,647,871 A | 7/1997 | Levine et al. |
| 5,342,409 A | 8/1994 | Mullett | 5,651,780 A | 7/1997 | Jackson et al. |
| 5,348,554 A | 9/1994 | Imran et al. | 5,658,322 A | 8/1997 | Fleming |
| 5,370,645 A | 12/1994 | Klicek et al. | 5,660,567 A | 8/1997 | Nierlich et al. |
| 5,370,672 A | 12/1994 | Fowler et al. | 5,688,267 A | 11/1997 | Panescu et al. |
| 5,370,675 A | 12/1994 | Edwards et al. | 5,690,692 A | 11/1997 | Fleming |
| 5,372,596 A | 12/1994 | Klicek et al. | 5,693,042 A | 12/1997 | Boiarski et al. |
| 5,383,874 A | 1/1995 | Jackson | 5,695,494 A | 12/1997 | Becker |
| 5,383,876 A | 1/1995 | Nardella | 5,696,351 A | 12/1997 | Benn et al. |
| 5,383,917 A | 1/1995 | Desai et al. | 5,702,386 A | 12/1997 | Stern et al. |
| 5,385,148 A | 1/1995 | Lesh et al. | 5,702,429 A | 12/1997 | King |
| 5,396,062 A | 3/1995 | Eisentraut et al. | 5,707,369 A | 1/1998 | Vaitekunas et al. |
| 5,400,267 A | 3/1995 | Denen et al. | 5,713,896 A | 2/1998 | Nardella |
| 5,403,311 A | 4/1995 | Abele et al. | 5,720,744 A | 2/1998 | Eggleston et al. |
| 5,403,312 A | 4/1995 | Yates et al. | D393,067 S | 3/1998 | Geary et al. |
| 5,409,000 A | 4/1995 | Imran | 5,722,975 A | 3/1998 | Edwards et al. |
| 5,409,006 A | 4/1995 | Buchholtz et al. | 5,733,281 A | 3/1998 | Nardella |
| 5,409,485 A | 4/1995 | Suda | 5,749,869 A | 5/1998 | Lindenmeier et al. |
| 5,413,573 A | 5/1995 | Koivukangas | 5,749,871 A | 5/1998 | Hood et al. |
| 5,417,719 A | 5/1995 | Hull et al. | 5,755,715 A | 5/1998 | Stern |
| 5,422,567 A | 6/1995 | Matsunaga | 5,766,165 A | 6/1998 | Gentelia et al. |
| 5,423,808 A | 6/1995 | Edwards et al. | 5,769,847 A | 6/1998 | Panescu |
| 5,423,809 A | 6/1995 | Klicek | 5,772,659 A | 6/1998 | Becker et al. |
| 5,423,810 A | 6/1995 | Goble et al. | 5,792,138 A | 8/1998 | Shipp |
| 5,430,434 A | 7/1995 | Lederer et al. | 5,797,802 A | 8/1998 | Nowak |
| 5,432,459 A | 7/1995 | Thompson | 5,797,902 A | 8/1998 | Netherly |
| 5,433,739 A | 7/1995 | Sluijter et al. | 5,814,092 A | 9/1998 | King |
| 5,434,398 A | 7/1995 | Goldberg | 5,817,093 A | 10/1998 | Williamson, IV et al. |
| 5,436,566 A | 7/1995 | Thompson | 5,820,568 A | 10/1998 | Willis |
| 5,438,302 A | 8/1995 | Goble | 5,827,271 A | 10/1998 | Buysse et al. |
| 5,443,463 A | 8/1995 | Stern et al. | 5,830,212 A | 11/1998 | Cartmell |
| 5,445,635 A | 8/1995 | Denen | 5,836,943 A | 11/1998 | Miller, III |
| 5,451,224 A | 9/1995 | Goble et al. | 5,836,990 A | 11/1998 | Li |
| 5,458,597 A | 10/1995 | Edwards et al. | 5,846,236 A | 12/1998 | Lindenmeier et al. |
| 5,462,521 A | 10/1995 | Brucker et al. | 5,868,737 A | 2/1999 | Taylor et al. |
| 5,472,441 A | 12/1995 | Edwards et al. | 5,868,739 A | 2/1999 | Lindenmeier et al. |
| 5,472,443 A | 12/1995 | Cordis et al. | 5,868,740 A | 2/1999 | LeVeen et al. |
| 5,478,303 A | 12/1995 | Foley-Nolan et al. | 5,871,481 A | 2/1999 | Kannenberg et al. |
| 5,480,399 A | 1/1996 | Hebborn | 5,897,552 A | 4/1999 | Edwards et al. |
| 5,483,952 A | 1/1996 | Aranyi | 5,908,444 A | 6/1999 | Azure |

| | | | | | | |
|---|---|---|---|---|---|---|
| 5,913,882 A | 6/1999 | King | | 6,575,969 B1 | 6/2003 | Rittman, III et al. |
| 5,921,982 A | 7/1999 | Lesh et al. | | 6,620,157 B1 | 9/2003 | Dabney et al. |
| 5,925,070 A | 7/1999 | King et al. | | 6,623,423 B1 | 9/2003 | Sakurai |
| 5,931,836 A | 8/1999 | Hatta et al. | | 6,635,057 B1 | 10/2003 | Harano |
| 5,938,690 A | 8/1999 | Law et al. | | 6,648,883 B1 | 11/2003 | Francischelli |
| 5,948,007 A | 9/1999 | Starkebaum et al. | | 6,652,514 B1 | 11/2003 | Ellman |
| 5,951,545 A | 9/1999 | Schilling | | 6,663,623 B1 | 12/2003 | Oyama et al. |
| 5,951,546 A | 9/1999 | Lorentzen | | 6,663,624 B1 | 12/2003 | Edwards |
| 5,954,686 A | 9/1999 | Garito et al. | | 6,666,860 B1 | 12/2003 | Takahashi |
| 5,954,717 A | 9/1999 | Behl et al. | | 6,679,875 B1 | 1/2004 | Honda |
| 5,961,344 A | 10/1999 | Rosales et al. | | 6,685,700 B1 | 2/2004 | Behl |
| 5,971,980 A | 10/1999 | Sherman | | 6,685,701 B1 | 2/2004 | Orszulak et al. |
| 5,976,128 A | 11/1999 | Schilling et al. | | 6,685,703 B1 * | 2/2004 | Pearson et al. ............... 606/41 |
| 5,983,141 A | 11/1999 | Sluijter et al. | | 6,692,489 B1 | 2/2004 | Heim |
| 6,010,499 A | 1/2000 | Cobb | | 6,712,813 B1 | 3/2004 | Ellman |
| 6,014,581 A | 1/2000 | Whayne et al. | | 6,730,080 B1 | 5/2004 | Harano |
| 6,033,399 A | 3/2000 | Gines | | 6,733,495 B1 | 5/2004 | Bek |
| 6,044,283 A | 3/2000 | Fein et al. | | 6,733,498 B1 | 5/2004 | Paton |
| 6,053,910 A | 4/2000 | Fleenor | | 6,740,079 B1 | 5/2004 | Eggers |
| 6,053,912 A | 4/2000 | Panescu et al. | | 6,740,085 B1 | 5/2004 | Hareyama |
| 6,056,745 A | 5/2000 | Panescu et al. | | 6,746,284 B1 * | 6/2004 | Spink, Jr. ................... 439/740 |
| 6,056,746 A | 5/2000 | Goble et al. | | 6,783,523 B1 | 8/2004 | Qin |
| 6,063,075 A | 5/2000 | Mihori | | 6,790,206 B1 | 9/2004 | Panescu |
| 6,063,078 A | 5/2000 | Wittkampf | | 6,796,981 B1 | 9/2004 | Wham |
| 6,068,627 A | 5/2000 | Orszulak et al. | | 6,824,539 B1 | 11/2004 | Novak |
| 6,074,386 A | 6/2000 | Goble et al. | | 6,830,569 B1 | 12/2004 | Thompson |
| 6,093,186 A | 7/2000 | Goble | | 6,835,082 B1 * | 12/2004 | Gonnering ................. 439/218 |
| RE36,871 E | 9/2000 | Epstein | | 6,843,789 B1 | 1/2005 | Goble |
| 6,113,591 A | 9/2000 | Whayne et al. | | 6,849,073 B1 | 2/2005 | Hoey |
| 6,113,596 A | 9/2000 | Hooven | | 6,855,141 B1 | 2/2005 | Lovewell |
| 6,123,702 A | 9/2000 | Swanson et al. | | 6,855,142 B1 | 2/2005 | Harano |
| 6,132,429 A | 10/2000 | Baker | | 6,860,881 B1 | 3/2005 | Sturm |
| 6,142,992 A | 11/2000 | Cheng et al. | | 6,864,686 B1 | 3/2005 | Novak |
| 6,162,217 A | 12/2000 | Kannenberg et al. | | 6,875,210 B1 | 4/2005 | Refior |
| 6,203,541 B1 | 3/2001 | Keppel | | D505,390 S * | 5/2005 | Lee et al. ................. D13/133 |
| 6,210,403 B1 | 4/2001 | Klicek | | 6,893,435 B1 | 5/2005 | Goble |
| 6,228,080 B1 | 5/2001 | Gines | | 2001/0014804 A1 | 8/2001 | Goble et al. |
| 6,228,081 B1 | 5/2001 | Goble | | 2001/0031962 A1 | 10/2001 | Eggleston |
| 6,231,569 B1 | 5/2001 | Bek | | 2002/0035353 A1 | 3/2002 | Edwards et al. |
| 6,238,387 B1 | 5/2001 | Miller, III | | 2002/0035364 A1 | 3/2002 | Schoenman et al. |
| 6,238,388 B1 | 5/2001 | Ellman | | 2002/0068932 A1 | 6/2002 | Edwards |
| 6,241,725 B1 | 6/2001 | Cosman | | 2002/0193787 A1 | 12/2002 | Qin |
| 6,245,065 B1 | 6/2001 | Panescu | | 2003/0004510 A1 | 1/2003 | Wham et al. |
| 6,246,912 B1 | 6/2001 | Sluijter et al. | | 2003/0060818 A1 | 3/2003 | Kannenberg |
| 6,251,106 B1 | 6/2001 | Becker et al. | | 2003/0078572 A1 | 4/2003 | Pearson et al. |
| 6,258,085 B1 | 7/2001 | Eggleston | | 2003/0139741 A1 | 7/2003 | Goble et al. |
| 6,261,285 B1 | 7/2001 | Novak | | 2003/0153908 A1 | 8/2003 | Goble |
| 6,273,886 B1 | 8/2001 | Edwards | | 2003/0163123 A1 | 8/2003 | Goble |
| 6,275,786 B1 | 8/2001 | Daners | | 2003/0163124 A1 | 8/2003 | Goble |
| 6,293,941 B1 | 9/2001 | Strul | | 2003/0171745 A1 | 9/2003 | Francischelli |
| 6,306,131 B1 | 10/2001 | Hareyama et al. | | 2003/0199863 A1 | 10/2003 | Swanson |
| 6,306,134 B1 | 10/2001 | Goble et al. | | 2004/0002745 A1 | 1/2004 | Flemming |
| 6,309,386 B1 | 10/2001 | Bek | | 2004/0019347 A1 | 1/2004 | Sakurai |
| 6,337,998 B1 | 1/2002 | Behl et al. | | 2004/0024395 A1 | 2/2004 | Ellman |
| 6,338,657 B1 * | 1/2002 | Harper et al. ............... 439/692 | | 2004/0030328 A1 | 2/2004 | Eggers |
| 6,358,245 B1 | 3/2002 | Edwards | | 2004/0030330 A1 * | 2/2004 | Brassell et al. ............... 606/41 |
| 6,383,183 B1 | 5/2002 | Sekino et al. | | 2004/0044339 A1 | 3/2004 | Beller |
| 6,398,779 B1 | 6/2002 | Buysse et al. | | 2004/0049179 A1 | 3/2004 | Francischelli |
| 6,398,781 B1 | 6/2002 | Goble et al. | | 2004/0054365 A1 | 3/2004 | Goble |
| 6,402,741 B1 | 6/2002 | Keppel et al. | | 2004/0068304 A1 | 4/2004 | Paton |
| 6,402,743 B1 | 6/2002 | Orszulak et al. | | 2004/0082946 A1 | 4/2004 | Malis |
| 6,436,096 B1 | 8/2002 | Hareyama | | 2004/0097912 A1 | 5/2004 | Gonnering |
| 6,451,015 B1 | 9/2002 | Rittman, III et al. | | 2004/0097914 A1 | 5/2004 | Pantera |
| 6,458,121 B1 | 10/2002 | Rosenstock | | 2004/0097915 A1 | 5/2004 | Refior |
| 6,464,689 B1 | 10/2002 | Qin | | 2004/0116919 A1 | 6/2004 | Heim |
| 6,464,696 B1 | 10/2002 | Oyama | | 2004/0133189 A1 | 7/2004 | Sakurai |
| 6,506,189 B1 | 1/2003 | Rittman, III et al. | | 2004/0138653 A1 | 7/2004 | Dabney |
| 6,508,815 B1 | 1/2003 | Strul | | 2004/0138654 A1 | 7/2004 | Goble |
| 6,511,476 B1 | 1/2003 | Hareyama | | 2004/0172016 A1 | 9/2004 | Bek |
| 6,547,786 B1 | 4/2003 | Goble | | 2004/0230189 A1 | 11/2004 | Keppel |
| 6,562,037 B1 | 5/2003 | Paton | | 2004/0243120 A1 | 12/2004 | Orszulak et al. |
| 6,565,559 B1 | 5/2003 | Eggleston | | 2004/0260279 A1 | 12/2004 | Goble |
| 6,573,248 B1 | 6/2003 | Ramasamy et al. | | 2005/0004564 A1 | 1/2005 | Wham |

| | | | |
|---|---|---|---|
| 2005/0021022 A1 | 1/2005 | Sturm et al. | |
| 2005/0101951 A1 | 5/2005 | Wham | |
| 2005/0113818 A1 | 5/2005 | Sartor | |
| 2005/0113819 A1 | 5/2005 | Wham | |
| 2005/0149151 A1 | 7/2005 | Orszulak | |
| 2005/0182398 A1 | 8/2005 | Paterson | |
| 2005/0197659 A1 | 9/2005 | Bahney | |
| 2005/0203504 A1 | 9/2005 | Wham et al. | |
| 2006/0025760 A1 | 2/2006 | Podhajsky | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 19717411 A1 | 11/1998 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 1293171 | 3/2003 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 855459 | 11/1960 |
| GB | 2164473 | 3/1986 |
| GB | 2214430 | 9/1989 |
| SU | 166452 | 1/1965 |
| SU | 747201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO 03/092520 | 11/2003 |
| WO | WO 05/060365 | 11/2003 |
| WO | WO 04/028385 | 4/2004 |
| WO | WO 04/098385 | 4/2004 |
| WO | WO 05/046496 | 5/2005 |
| WO | WO 05/048809 | 6/2005 |
| WO | WO 05/050151 | 6/2005 |

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic computerized Bipolar Coagulator" Journal of Neurosurgery 75:1, (Jul., 1991) pp. 148-151.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedence" Am. J. Ml, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp.

Vallfors et al., "Automatically Controlled Bipolar Electrosoagulation-'COA-COMP'" Neurosurgical Review 7:2-3 (1984) pp. 187-190.

Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp.

Chicharo et al. "A Sliding Goertzel Algorith" Aug. 1996, pp. 283-297 Signal Processing, Elsevier Science Publishers B.V. Amsterdam, NL. vol. 52 No. 3.

Ogden "Goertzel Alternative to the Fourier Transform" Jun. 1993 pp. 485-487 Electronics World; Reed Business Publishing, Sutton, Surrey, GB vol. 99, No. 1687.

International Search Report—PCT/US03/37310.
International Search Report—PCT/US03/37110.
International Search Report—PCT/US03/37310.
International Search Report—EP4009964.
International Search Report—EP98300964.8.
International Search Report—EP04015981.6.

Ogden Goertzel Alternative to the Fourier Transform: Jun. 1993 pp. 485-487 Electronics World; Reed Business Publishing, Sutton, Surrey, BG vol. 99, No. 9, 1687.

Medtrex Brochure "The O.R. Pro 300" 1 p. Sep. 1998.

Valleylab Brochure "Valleylab Electroshield Monitoring System" 2 pp. Nov. 1995.

Richard Wolf Medical Instruments Corp. Brochure, "Kleppinger Bipolar Forceps & Bipolar Generator" 3 pp. Jan. 1989.

Bergdahl et al. "Studies on Coagulation and the Development of an Automatic Computerized Bipolar Coagulator" J. Neurosurg, vol. 75, Jul. 1991, pp. 148-151.

International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.

* cited by examiner

CONNECTOR SYSTEMS FOR ELECTROSURGICAL GENERATOR

BACKGROUND

1. Technical Field

The present disclosure relates to electrosurgical instrument systems and, more particularly, to connector systems for selectively connecting electrosurgical instruments and electrosurgical generators to one another.

2. Background

Electrosurgical instrument systems have become widely used by surgeons in recent years. Accordingly, a need has developed for equipment that is easy to handle and operate, is reliable and is safe. By and large, most electrosurgical instrument systems typically include a hand-held electrosurgical instrument or pencil electrically connected to a source of electrosurgical energy (e.g., an electrosurgical generator). The electrosurgical instrument transfers radio-frequency (RF) electrical energy to a tissue site. The electrosurgical energy is returned to the electrosurgical generator via a return electrode pad positioned under a patient (i.e., a monopolar system configuration) or a smaller return electrode positionable in bodily contact with or immediately adjacent to the surgical site (i.e., a bipolar system configuration). The waveforms produced by the electrosurgical generator yield a predetermined electrosurgical effect known generally as electrosurgical fulguration.

Recently, electrosurgical instrument systems have been increasingly provided with coupling and/or connecting systems (e.g., a plug) for removably connecting the electrosurgical instrument to the electrosurgical generator. Typically, the electrosurgical instrument is provided with a so called "male" connector while the electrosurgical generator is provided with the corresponding "female" connector.

Since electrosurgery requires controlled application of radio frequency energy to an operative tissue site, it is important that the appropriate electrosurgical generator be correctly and/or properly mated with the electrosurgical instrument for the specific electrosurgical procedure. Due to the variety of operative, electrosurgical procedures, requiring various levels of radio frequency energy delivery from an attached instrument, issues arise with the mismatching of electrosurgical instruments and electrosurgical generators.

Accordingly, a need exists for a connecting system, for electrosurgical generators which allow various surgical instruments to be selectively connected to corresponding electrosurgical generators.

SUMMARY

The present disclosure relates to connector systems for connecting an electrosurgical instrument to an electrosurgical generator. According to one particularly advantageous embodiment of the present disclosure, the connector system includes a plug portion connected to the electrosurgical instrument and including a profile or shape which is selectively mateable with a plug receptacle portion. Advantageously, the plug receptacle portion is retained in the electrosurgical generator and is backward compatible, i.e., able to receive both old flying lead electrosurgical instruments or 2-pin, 3-pin or 4-pin electrical instruments and able to selectively receive enhanced surgical devices with multiple electrical connections.

In one embodiment, the plug portion includes a plug housing having a power pin extending therefrom. The power pin is advantageously positioned closer to a first side edge of the plug housing than a second side edge thereof, wherein the second side edge is opposite the first side edge.

Advantageously, the plug portion includes at least one position pin extending from the plug housing. Preferably, a first position pin extends from a center of the plug housing in substantially the same direction as the power pin. A second position pin may be included which extends from the plug housing at a location off-set from the center thereof and in the same direction as the power pin.

The connector system may also advantageously include a prong extending from the plug housing and substantially in the same direction as the power pin. The prong is desirably positioned closer to a first side edge of the plug housing than a second side edge thereof, wherein the second side edge is opposite the first side edge thereof.

The prong preferably includes a plurality of electrical contacts which provide electrical continuity to the electrosurgical generator. In one embodiment, the prong has a generally L-shaped cross-sectional profile for use with a six (6) contact electrosurgical system. In another embodiment, the prong has a generally rectilinear cross section or profile for use with a four (4) contact system. Advantageously, the L-shaped cross-sectional profile blocks insertion of a plug portion into the plug receptacle portion which is upside down. Other shapes are also envisioned, e.g., generally rectangular, for lesser contact systems, e.g., a four (4) contact system.

Preferably, the plug receptacle portion is operatively retained in the electrosurgical generator and defines a recess for receipt of the plug portion therein. The plug receptacle portion advantageously includes a prong receptacle formed therein, the prong receptacle being shaped and dimensioned to receive the prong therein. It is envisioned that the plug receptacle portion can include a plurality of apertures formed therein for receiving the power pin and the position pins. Preferably, each aperture includes a contact terminal operatively associated therewith. The plug receptacle portion advantageously includes at least one contact pin extending therethrough which is positioned to contact a respective one of the electrical contacts of the prong.

The prong desirably has an overall width which is less than about 0.43 inches and an overall height which is less than about 0.38 inches for the L-shaped six (6) contact prong. For prongs with less than six (6) contacts, e.g., four (4) contacts, the overall height may be less. The prong receptacle desirably has an overall width which is greater than about 0.39 inches and an overall height which is greater than about 0.324 inches.

In one embodiment of the connector system, the connector system includes a tactile feedback mechanism which provides positive tactile feedback to the user that the plug portion has been properly inserted into the plug receptacle portion. Advantageously, the tactile feedback mechanism includes a first post extending through and pivotally supported on the plug receptacle portion and a second post extending through and supported on the plug receptacle portion. Preferably, the first post is spring biased. The tactile feedback mechanism also includes a linkage member which extends between the first post and the second post. The linkage member includes a first arm which extends radially from the first post and a second arm which is supported on and extends from the second post.

A camming pin extends through a distal end of the first arm. The camming pin preferably includes a first portion slidably receivable in an elongate slot formed in the second arm. A second portion is slidably received in an arcuate slot formed in the prong receptacle. The second portion is extendable to engage a groove formed in a lower surface of the prong. A spring is positioned to bias the first portion to a distal-most position in the elongate slot.

In one embodiment, the plug portion includes symbology provided on a surface thereof which includes information regarding the operative parameters of the electrosurgical instrument.

The present disclosure also relates to a connector system for connecting an electrosurgical instrument to an electrosurgical generator which includes a plug portion and a plug receptacle portion disposed on the generator. The plug portion includes a plurality of mechanical interfaces which selectively mate with a corresponding plurality of mechanical interfaces in the plug receptacle portion. A tactile feedback mechanism is included for providing positive feedback to the user that the mechanical interfaces of the plug portion have been properly mated with the corresponding mechanical interfaces of the plug receptacle portion.

The tactile feedback mechanism includes a pair of first and second posts extending through and pivotally supported on the plug receptacle portion and a linkage member extending between the first post and the second post. The linkage member has a first arm extending radially from the first post and a second arm supported on and extending from the second post. A camming pin is included which extends through a distal end of the first arm. Upon insertion of the plug portion into the receptacle portion, the camming pin rides along a slot disposed in the second arm to initially compress a spring. After a predetermined point of the camming pin riding along the slot, the spring subsequently expands to drive the camming pin through the slot thus towing the prong portion into prong receptacle portion.

Other objects and features of the present disclosure will become apparent from consideration of the following description taken in conjunction with the accompanying drawings.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

DETAILED DESCRIPTION

Figure 1:
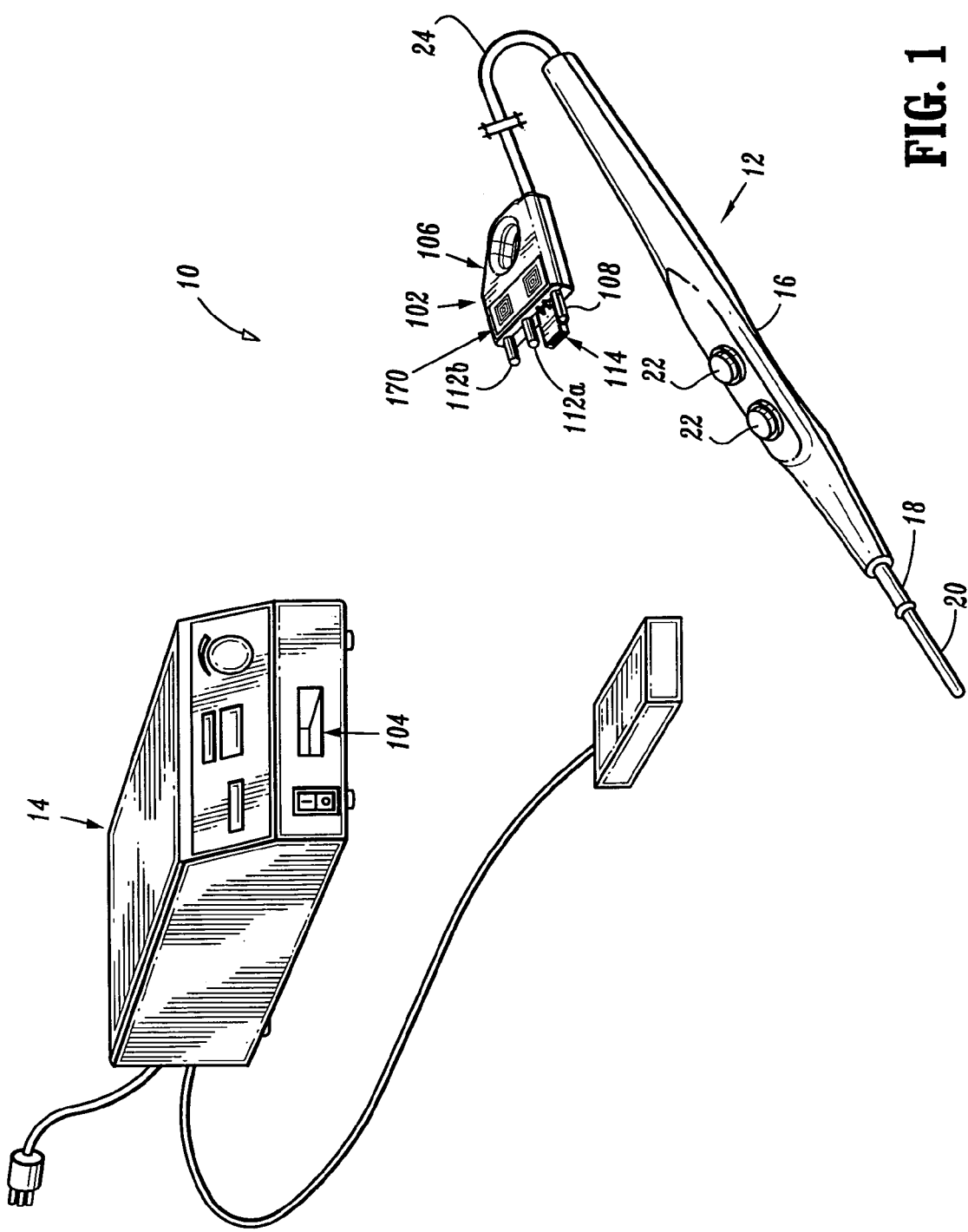
FIG. 1 is a schematic illustration of an electrosurgical instrument system in accordance with the present disclosure.

Embodiments of the presently disclosed connector system for electrosurgical generators are described in detail herein with reference to the drawing figures wherein like reference numerals identify similar or identical elements. In the drawings and in the description which follows, the term "proximal", as is traditional, will refer to the end of the apparatus and/or device which is closest to the operator, while the term "distal" will refer to the end of the apparatus and/or device which is furthest from the operator.

Referring initially to FIG. 1, there is seen a perspective view of an electrosurgical instrument system in accordance with an exemplary embodiment of the present disclosure, generally indicated as reference numeral 10. Electrosurgical instrument system 10 includes an electrosurgical instrument 12 (e.g., an electrosurgical pencil) which is electrically connectable to a source of electrosurgical energy 14 (e.g., an electrosurgical generator).

Electrosurgical pencil 12 includes a housing 16 configured and adapted to support a blade receptacle 18 at a distal end thereof which, in turn, receives a replaceable electrocautery blade 20 therein. Electrosurgical pencil 12 further includes at least one activation button 22 supported on an outer surface of housing 16. Activation button(s) 22 are operable to control the supply of RF electrical energy to blade 20 from electrosurgical generator 14.

By way of example only, electrosurgical generator 14 may be any one of the following, or equivalents thereof: the "FORCE FX", "FORCE 2" or "FORCE 4" generators manufactured by Valleylab, Inc. of Boulder, Colo. It is contemplated that electrosurgical generator 14 can be preset to selectively provide an appropriate first predetermined RF signal (e.g., about 1 to 300 watts) for tissue cutting and an appropriate second predetermined RF signal (e.g., about 1 to 120 watts) for tissue coagulation. However, as will be described in greater detail below, electrosurgical generator 14 preferably is adapted to automatically configure itself to transmit particular RF signals depending on the particular electrosurgical instrument connected thereto.

Figure 2:
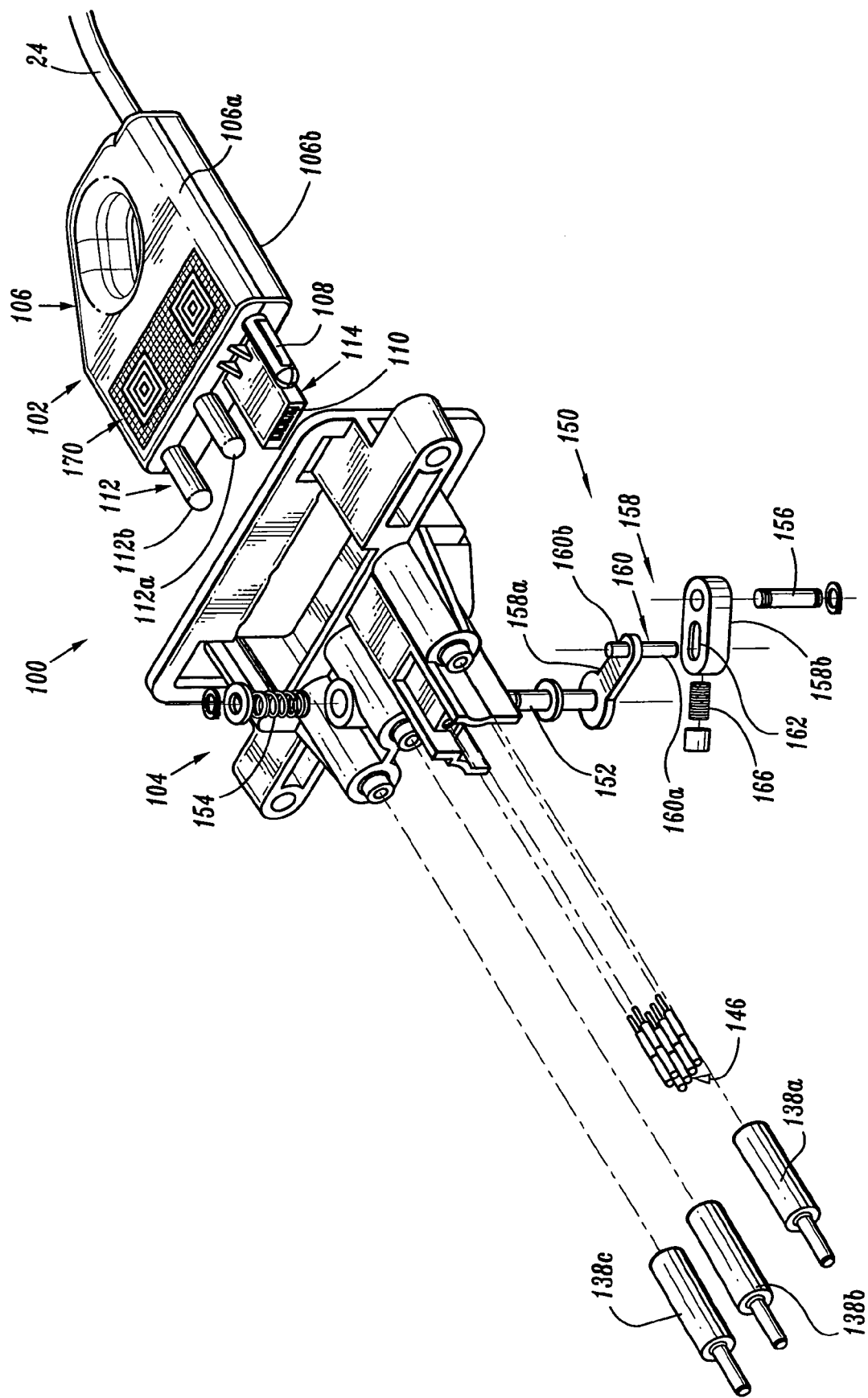
FIG. 2 is an enlarged perspective view of a connector system, in accordance with an embodiment of the present disclosure, as seen from above.

As seen in FIGS. 1–9, electrosurgical instrument system 10 is provided with a connector system 100, as best seen in FIG. 2, which is configured and adapted to selectively connect particular electrosurgical instruments (e.g., electrosurgical pencils 12) to particular sources of electrosurgical energy (e.g., electrosurgical generators 14). Connector system 100 includes a plug or male portion 102 operatively associated with electrosurgical instrument 12 via a connecting wire 24 and a receptacle, socket or female portion 104 which is operatively associated with electrosurgical generator 14. Preferably, receptacle portion 104 is "backward compatible", i.e., able to receive or connect to plug portions 102 of the various electrosurgical instruments disclosed herein as well as able to receive or connect other prior electrosurgical instruments which include less pins or prongs.

Figure 4:
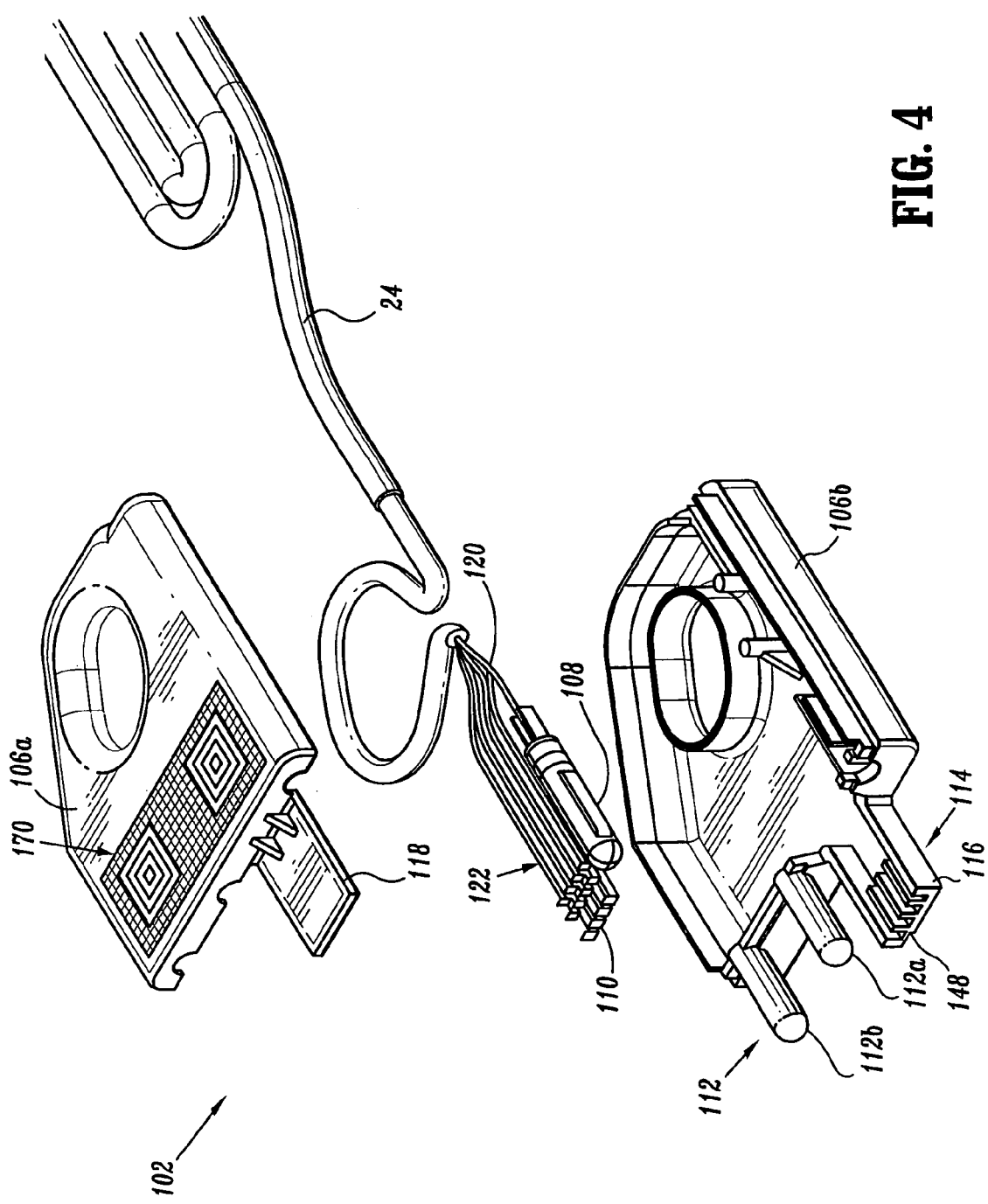
FIG. 4 is an enlarged exploded perspective view of the plug portion of the connector system of FIGS. 2–3.

With reference to FIG. 4, plug portion 102 includes a housing portion 106 having a first-half section 106a and a second half-section 106b operatively engagable with one another, preferably, via a snap-fit engagement. Half-sections 106a, 106b are configured and adapted to retain a common power pin 108 and a plurality of electrical contacts 110 therebetween, as will be described in greater detail below.

Plug portion 102 includes a power pin 108 extending distally from housing 106 at a location preferably between first half-section 106a and second half-section 106b. Preferably, power pin 108 is positioned to be off center, i.e., closer to one side edge of housing 106 than the other. Plug portion 102 further includes at least one, preferably, a pair of position pins 112 also extending from housing 106. Position pins 112 are preferably positioned between half-sections 106a and 106b and are oriented in the same direction as power pin 108. Desirably, a first position pin 112a is positioned in close proximity to a center of housing 106 and a second position pin 112b is positioned to be off center and in close proximity to an opposite side edge of housing 106 as compared to power pin 108. Pins 112a, 112b and 108 are preferably located on plug portion 102 at positions which correspond to the pin positions of earlier connections which are compatible to earlier known generators.

Plug portion 102 further includes a prong 114 extending from housing 106. In particular, prong 114 includes a body portion 116 (see FIG. 4) extending from second half-section 106b of housing 106 and a cover portion 118 extending from first half-section 106a of housing 106. In this manner, when half-sections 106a, 106b are joined to one another, cover portion 118 of prong 114 encloses body portion 116. Preferably, prong 114 is positioned between power pin 108 and first position pin 112a. Prong 114 is configured and adapted to retain electrical contacts 110 therein such that a portion of each contact 110 is exposed along a front or distal edge thereof. While four contacts 110 are shown, it is envisioned that any number of contacts 110 can be provided, including and not limited to two, six and eight. Prong 114 is dimensioned to have an overall width which is less than about 0.43 inches and an overall height which is less than about 0.38 inches.

With continued reference to FIG. 4, connecting wire 24 includes a power supplying wire 120 electrically connected to power pin 108 and a plurality of control wires 122 electrically connected to contacts 110.

Figure 5:
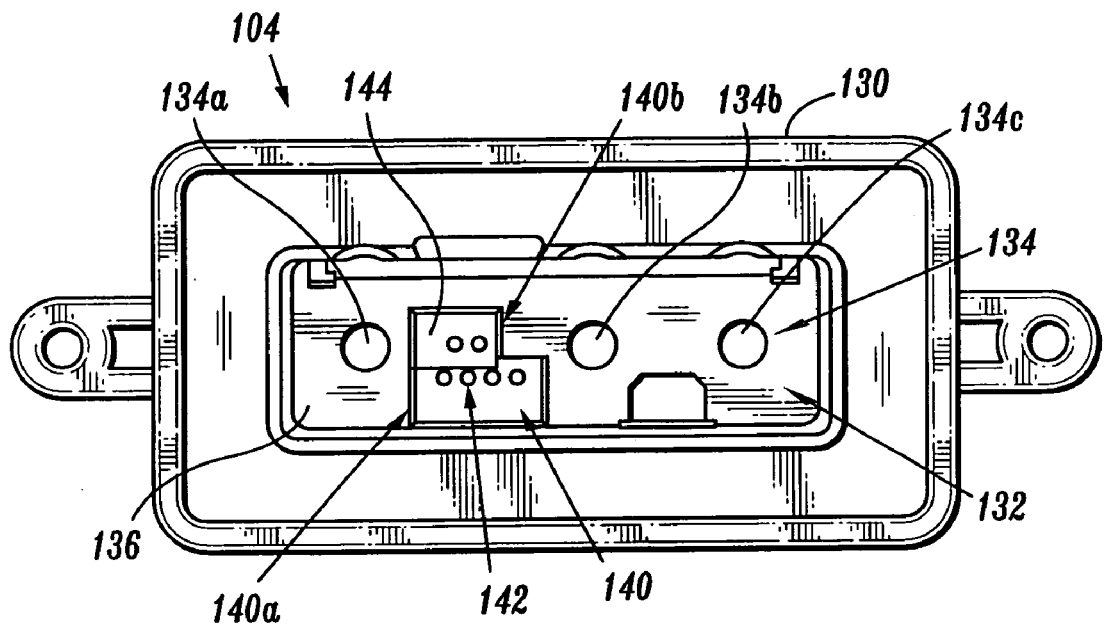
FIG. 5 is a front elevational view of the receptacle portion of the connector system of FIGS. 2–3.
Figure 6:
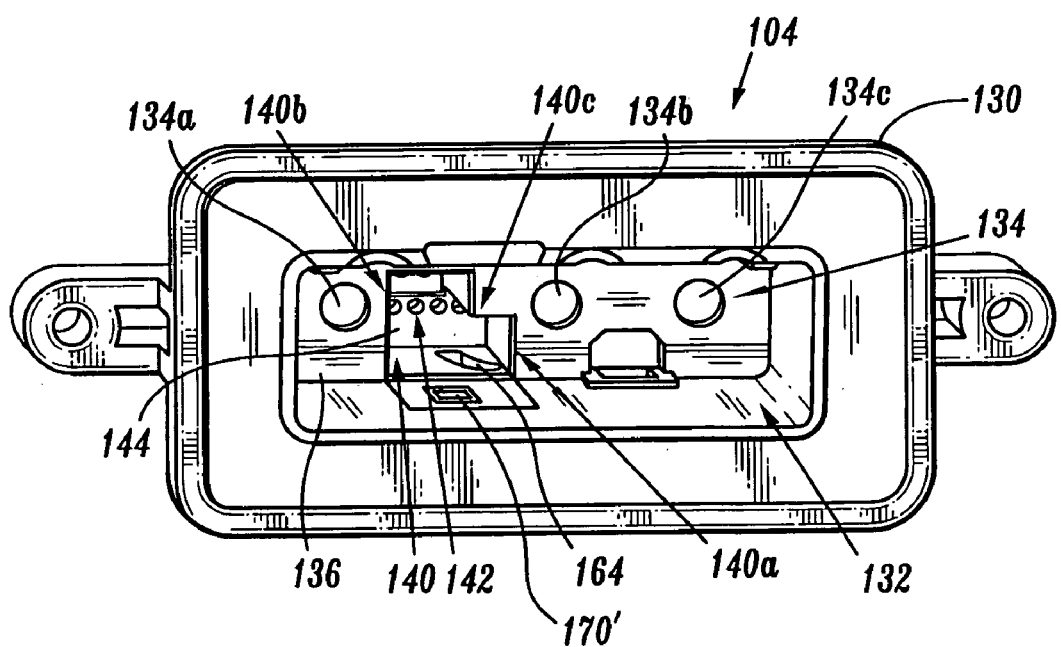
FIG. 6 is a front perspective view of the receptacle portion of the connector system of FIGS. 2–3.

With reference to FIGS. 2 and 5–6, receptacle portion 104 of connector system 100 includes a housing 130 having a recess 132 formed therein. Recess 132 is configured and dimensioned to receive plug portion 102 therein. Recess 132 includes a plurality of apertures 134 formed in a rear wall 136 thereof. Preferably, three apertures 134a–134c are provided. Apertures 134a–134c are preferably positioned and sized to respectively receive power pin 108 and position pins 112 therein when plug portion 102 is inserted into receptacle portion 104. As mentioned above, preferably, apertures 134a–134c are positioned to receive connector pins from prior known connectors to enable the connector system to be backward compatible.

Figure 7:
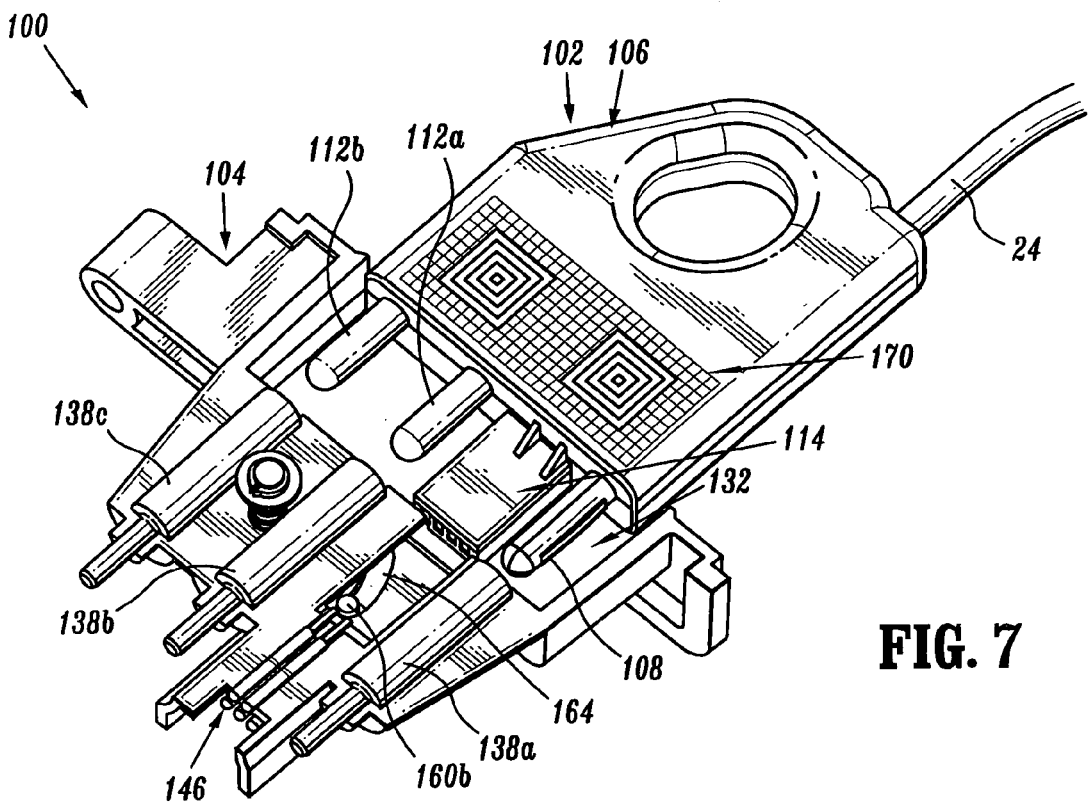
FIG. 7 is an enlarged top perspective view of connector system of FIGS. 2–3, with portions of the receptacle portion cut away, illustrating the mating and/or joining of the plug portion with the receptacle portion.
Figure 8:
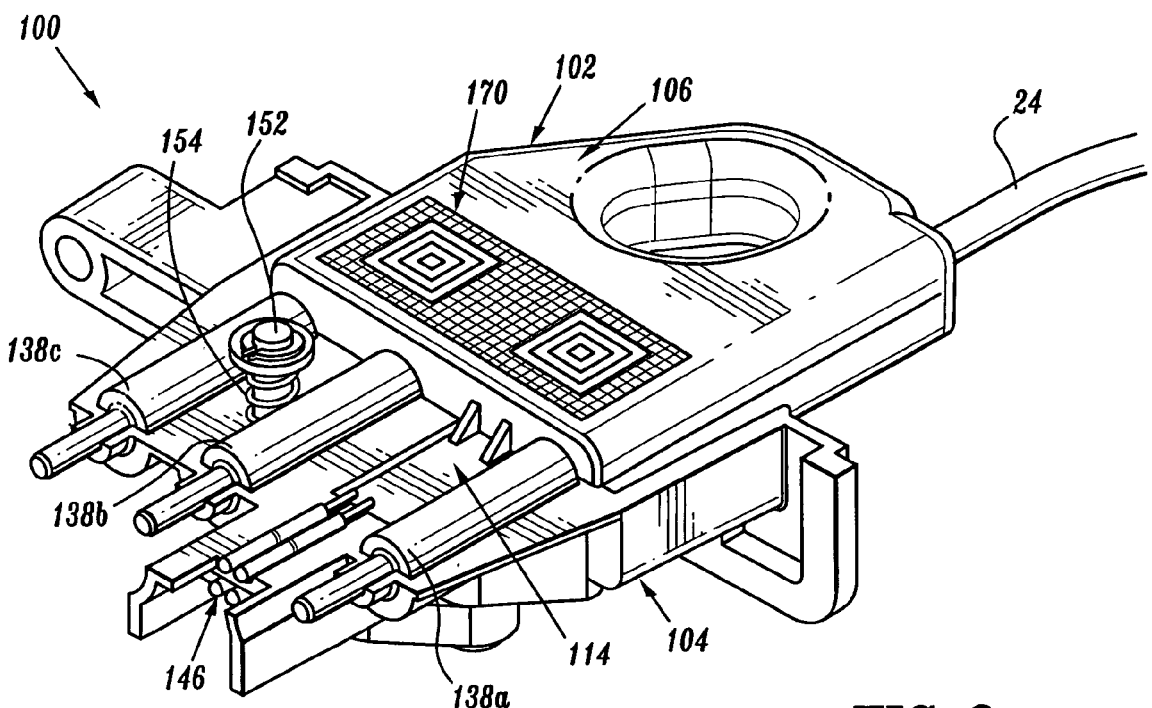
FIG. 8 is an enlarged top perspective view of the connector system of FIGS. 2–3, with portions of the receptacle portion cut away, illustrating the plug portion mated with the receptacle portion.
Figure 9:
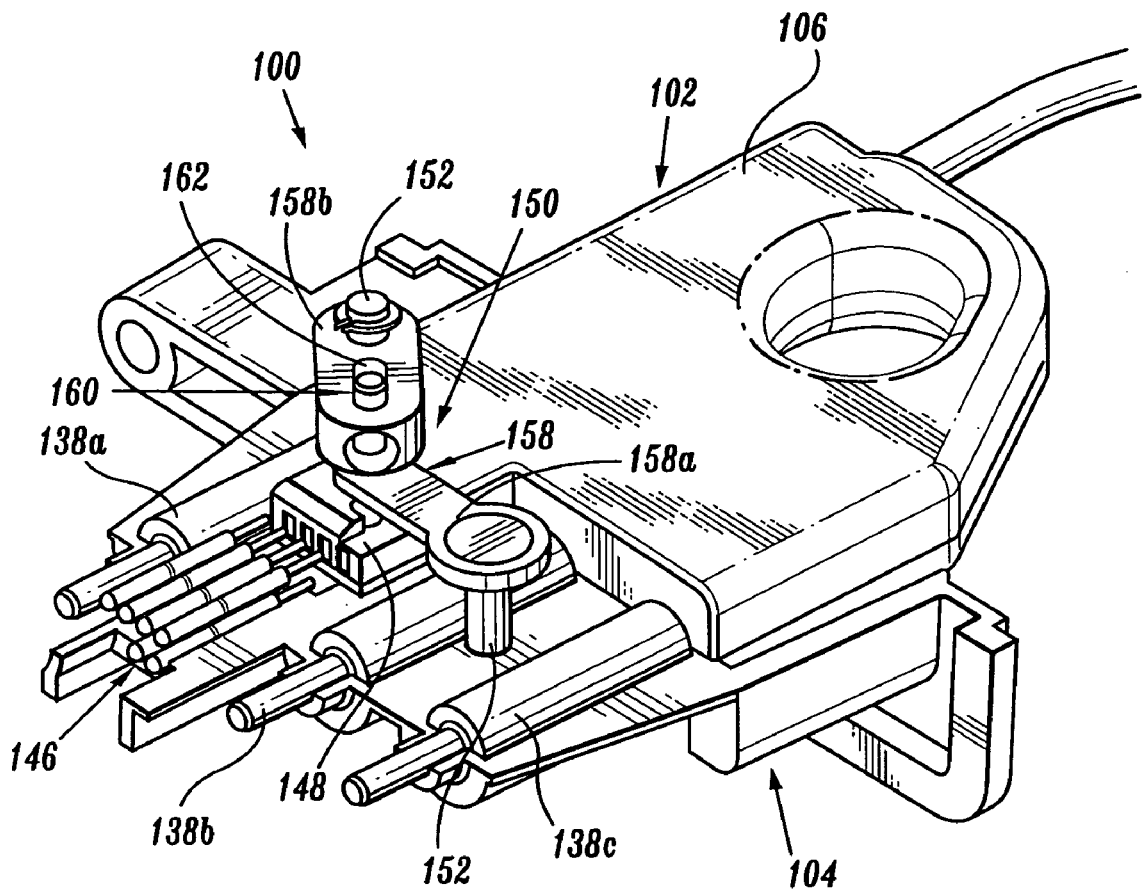
FIG. 9 is an enlarged bottom perspective view of the connector system of FIGS. 2–3, with portions of the receptacle portion broken away, illustrating the plug portion mated with the receptacle portion.

As seen in FIG. 2, and in greater detail in FIGS. 7–9, receptacle portion 104 further includes contact terminals 138a–138c disposed behind rear wall 136 and in registration with a respective aperture 134a–134c. Contact terminals 138a–138c are configured and dimensioned to receive power pin 108 and position pins 112 therein. While only contact terminal 138a needs to be configured and adapted to create an electrical interface with power pin 108, it is within the scope of the present disclosure to have each contact terminal 138a–138c configured and adapted to provide electrical interfaces. For example, contact terminals 138a–138c can be fabricated from an electrically conductive material such that when plug portion 102 is inserted into receptacle portion 104 and power pin 108 is inserted into corresponding contact terminal 138a through aperture 134a, contact terminal 138a electrically engages power pin 108 and, in turn, enables transmission of RF energy from electrosurgical generator 14 to electrosurgical instrument 12. One practicable example would be to utilize the positive engagement of pins 112a, 112b within the contact terminals 138a, 138b as a safety mechanism, i.e., pins 112a, 112b must be properly and fully seated within terminals 138a, 138b to allow the generator to supply energy to the instrument.

With continued reference to FIGS. 5 and 6, receptacle portion 104 further includes a prong receptacle 140 formed in rear wall 136. Prong receptacle 140 is preferably formed between apertures 134a and 134b. Prong receptacle 140 is sized and shaped to receive prong 114 therein when plug portion 102 is inserted into receptacle portion 104.

Since prong 114 extends from second half-section 106b of housing 106 of plug portion 102, plug portion 102 will not enter receptacle portion 104 unless plug portion 102 is in the proper orientation. In this manner, it is ensured that power pin 108 is in electrical contact with corresponding contact terminal 138a. As can be appreciated, connectors which do not include prongs 114 are still connectable to receptacle portion 104 (i.e., backward compatible). However, electrical contacts 110 associated with prong 114 are designed to further enhance the electrical connection between the instrument and the generator and give the surgeon more feedback at the operative site. For example, commonly-owned and concurrently-filed U.S. patent application No. [11697(203-3624)] entitled "ELECTROSURGICAL PENCIL WITH IMPROVED CONTROLS " and PCT Application Serial No. PCT/US03/22900 entitled "ELECTROSURGICAL PENCIL WITH DRAG SENSING CAPABILITY " describe several features which would typically utilize the additional electrical contacts 110 in prong 114 to enhance feedback to the surgeon at the operative site, e.g., mode or power settings or sensors for movement, position, drag or temperature.

Preferably, as seen in FIGS. 5 and 6, prong receptacle 140 includes a lower portion 140a configured and dimensioned to receive prong 114, as described above. Prong receptacle 140 is dimensioned to have an overall width which is greater than about 0.39 inches and an overall height which is greater than about 0.324 inches. It is envisioned that, prong receptacle 140 can further include an upper portion 140b which is integral with lower portion 140a and defines a prong receptacle 140 having an "L-shaped " cross-sectional profile. In this manner, prong receptacle 140 can receive prongs having any number of cross-sectional profiles, including and not limited to, rectangular (e.g. prong 114), square and "L-shaped " (see FIGS. 10 and 11). Moreover, "L-shaped " prong receptacle 140 defines a corner 140c which is shaped and sized to block the insertion of a traditional three pin plug when the traditional plug is being inserted upside down.

With continued reference to FIGS. 5 and 6, prong receptacle 140 includes a plurality of openings 142 formed in a rear wall 144 thereof for permitting passage of contact pins 146, preferably spring-type contact pins, therethrough. In this manner, when plug portion 102 is inserted into receptacle portion 104, electrical contacts 110 of prong 114 will electrically engage pins 146.

As best seen in FIG. 5, prong receptacle 140 can include four openings 142 formed in lower portion 140a and two openings 142 formed in upper portion 140b. While such an arrangement is shown and described, it is within the scope of the present disclosure to include various other arrangements including various numbers of pins 146.

With reference to FIGS. 2–9, connector system 100 further includes a tactile feedback mechanism 150 (see FIG. 9) for securing plug portion 102 into receptacle portion 104, for providing positive feedback to the user that plug portion 102 has been fully inserted into receptacle portion 104, and for compensating for increasing resistance that exists as prong 114 enters into prong receptacle 140 and engages pins 146.

Tactile feedback mechanism 150 includes a first post 152 extending through and pivotally supported on receptacle portion 104. Preferably, first post 152 is spring biased by a spring member 154. Tactile feedback mechanism 150 further includes a second post 156 extending through and supported on receptacle portion 104. A linkage member 158 extends between first post 152 and second post 156. Linkage member 158 includes a first arm 158a extending radially from first post 152 and a second arm 158b supported on and extending from second post 156.

Figure 3:
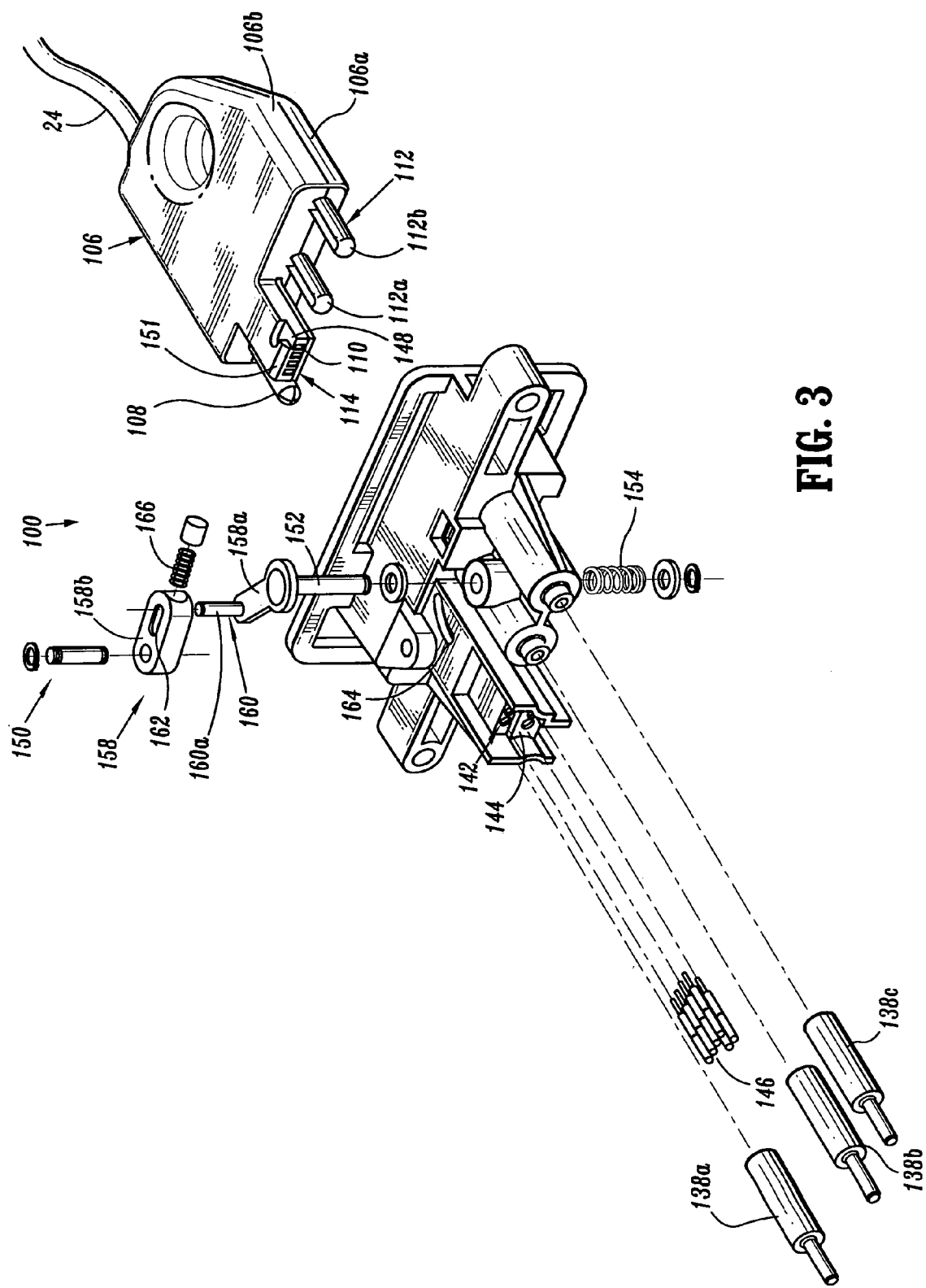
FIG. 3 is an enlarged perspective view of the connector system of FIG. 2, as seen from below.

A camming pin 160 extends through a distal end of first arm 158a and includes a first portion 160a which is slidably receivable in an elongate slot 162 (see FIG. 2) formed in second arm 158b and a second portion 160b, extending in an opposite direction to first portion 160a, which is slidably receivable in an arcuate slot 164 formed in prong receptacle 140 (see FIGS. 3, 6 and 7). First portion 160a is biased to the distal-most position of elongate slot 162 by a spring 166 disposed within second arm 158b. Second portion 160b extends through arcuate slot 164 an amount sufficient to be engagable with an "L-shaped" groove and/or recess 148 formed in a lower surface of prong 114 (see FIGS. 3, 4 and 9) in order to define a bayonet-type engagement. Alternatively, second arm 158b may extend "opposite" first post 152 and be joined by a tension spring (not shown) to first post 152.

In use, with camming pin 160 initially positioned near the entrance of prong receptacle 140, as prong 114 enters prong receptacle 140, second portion 160b of camming pin 160 enters into and engages groove 148 of prong 114. As prong 114 is further advanced, camming pin 160 rides along arcuate slot 164 and elongate slot 162, thereby compressing spring 166. Once prong 114 is advanced beyond a point of criticality, spring 166 expands and thus drives camming pin 160 through the remainder of arcuate slot 164 thereby drawing prong 114 into prong receptacle 140.

It is envisioned that spring 154 may provide an additional safety feature as well. For example, spring 154 is provided in pin 152 to allow a mating chamfer 153 on pin 152 (FIG. 12) to ride up and over the chamfer 151 (FIG. 3) on plug 102. This is necessitated to allow plug 102 to be inserted in the event that the cam is disengaged prior to being pulled back to the proximal position upon removal of the last plug 102 to have been inserted.

As seen in FIGS. 1, 2, 4 and 7–8, connector system 100 further includes symbology 170 provided on a surface of plug portion 102, preferably on an outer surface of first half-section 106a of housing 106. Symbology 170 can include and is not limited to at least one of the following: bar codes, UPC codes, Postnet. Data Matrix, Maxi Code, Aztec Code and the like. Preferably, symbology 170 includes at least one Aztec code, preferably, a pair of Aztec codes positioned side-by-side.

Aztec Code is a high density two dimensional matrix style bar code symbology that can encode up to 3750 characters from the entire 256 byte ASCII character set. The Aztec code symbol is built on a square grid with a bulls-eye pattern at its center. Data is encoded in a series of "layers" that circle around the bulls-eye pattern. Each additional layer completely surrounds the previous layer thus causing the symbol to grow in size as more data is encoded yet the symbol remains square.

In this manner, each electrosurgical instrument 12 is provided with a characteristic symbology 170 containing information regarding the operative parameters for that particular electrosurgical instrument, such as, for example, the operative RF energy setting, the operative waveform setting, and the algorithm for interpreting signals on contact(s) 110 and pin(s) 146.

Connector system 100 can further include a symbology reader and/or scanner (not shown) operatively supported in receptacle portion 104. Accordingly, when plug portion 102 is mated with receptacle portion 104, the reader scans and reads the operative parameters contained in the characteristic symbology 170 and transmits the operative parameters to electrosurgical generator 14 which in turn automatically configures and/or sets itself to supply operative parameters (e.g., preset ranges, preferred settings and the like) to electrosurgical instrument 12. Alternatively, electrosurgical generator 14 can be engaged with a data table which, once the instrument is identified, will transmit the appropriate RF parameter to the identified instrument. In addition, as described above, symbology 170 can also be used as a positive engagement mechanism. For example, the symbology must be aligned or in a position to allow the instrument to operate or to allow the instrument to operate in an enhanced mode.

For example and with respect to FIG. 6, receptacle 140 may contain additional symbology 170' on the interior surface opposite the scanner window similar to that on plug 12. The symbology 170' is positioned between the power pin and the next adjacent pin. The scanner will then read the symbology 170' whenever a plug is not inserted. When a plug is inserted, the symbology 170' will be blocked and the scanner will then read the symbology 170 on the plug 102 to determine pencil type and the appropriate electrosurgical settings associated that that particular pencil. If the symbology 170' is blocked but no new symbology 170 is identified, then the generator will determine that the plug 102 is of an old style pencil without enhanced capabilities (e.g., an E2525 or E2516 Electrosurgical Pencil sold by Valleylab—a division of Tyco Healthcare LP in Colorado). Old style pencils will respond to switch signals on pins 138b and 138c outputting RF on a pin 138 as called for by the surgeon. The symbology 170' in the receptacle is preferably positioned such that flying leads from existing devices will not obscure the symbology 170' and therefore will not enable the electrosurgical generator to output RF through pin 108.

It is envisioned that connector system 100 can include a positive engagement mechanism configured and adapted to ensure proper engagement of prong portion 102 in receptacle portion 104 prior to allowing activation of electrosurgical instrument 12. For example, the positive engagement mechanism may include an optical coupler pair (e.g., an optical coupler member operatively associated with prong portion 102 and a cooperating coupler member operatively associated with receptacle portion 104, for example, reflective diodes), mechanical coupler pairs, electromechanical coupler pairs, and/or bar code readers. In addition, the positive engagement mechanism can be configured and adapted to not be activated and/or triggered by insertion of "flying leads", from prior art instruments, into receptacle portion 104 thereby preventing activation of such instruments.

Figure 10:
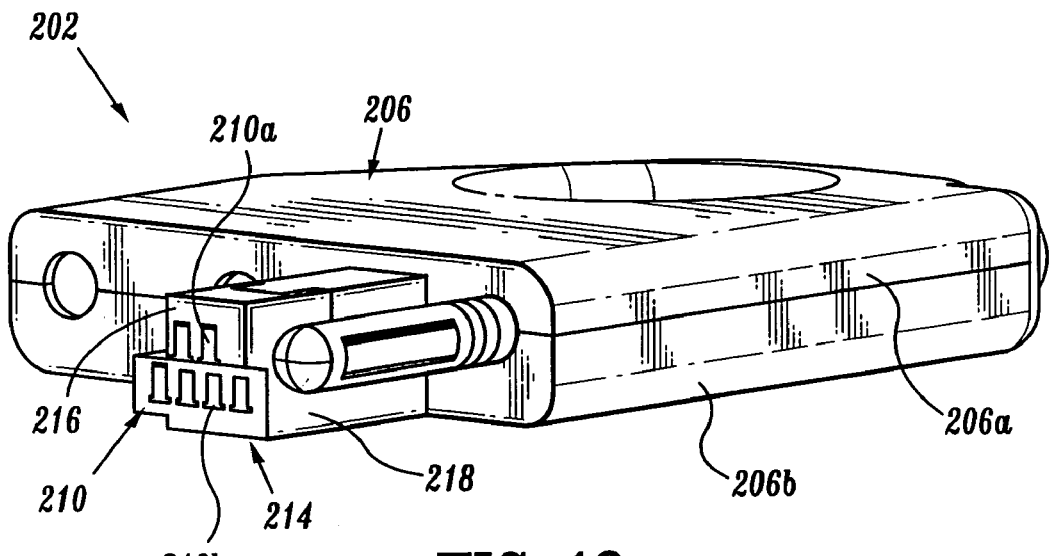
FIG. 10 is a perspective view of a plug portion in accordance with an alternate embodiment of the present disclosure, as seen from above.
Figure 11:
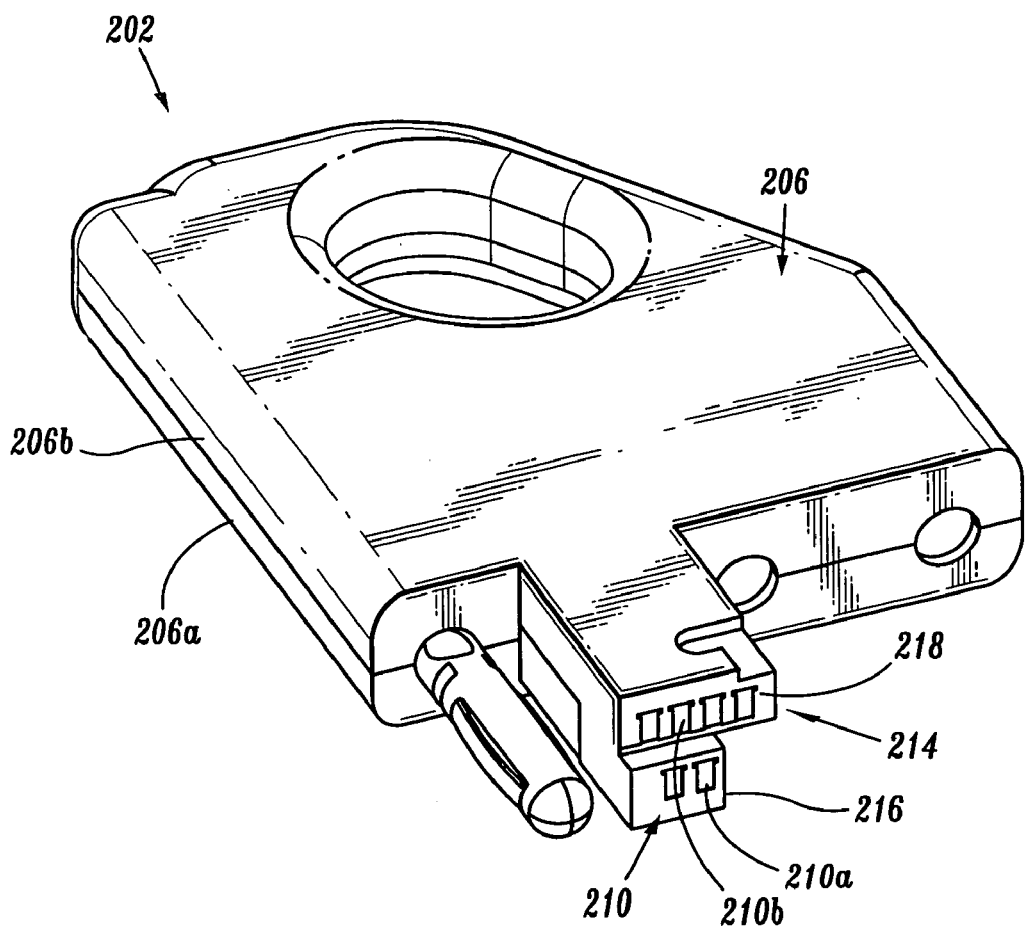
FIG. 11 is a perspective view of the plug portion of FIG. 10 as seen from below.

Turning now to FIGS. 10 and 11, a plug portion, in accordance with an alternate embodiment of the present disclosure, is designated generally as 202. Plug portion 202 is similar to plug portion 102 and will only be described in detail to the extent necessary to identify differences in construction and/or operation.

Plug portion 202 includes a prong 214 extending from housing 206. In particular, prong 214 includes a first portion 216 extending from first half-section 206a of housing 206 and a second portion 218 extending from second half-section 206b of housing 206. Preferably, second portion 218 of prong 214 has a width which is greater than a width of first portion 216. In this manner, when first and second half-sections 206a, 206b of housing 206 are joined to one another, prong 214 has an L-shaped transverse cross-sectional profile. In particular, prong 214 is configured and dimensioned to be received in complementary shaped prong receptacle 140 of receptacle portion 104 (see FIGS. 4 and 5).

Prong 214 includes a plurality of contacts 210 exposed along a front surface thereof. In particular, prong 214 includes a first set of contacts 210a, preferably two, exposed along a front surface of first portion 216 of prong 214 and a second set of contacts 210b, preferably, four, exposed along a front surface of second portion 218 of prong 214.

Accordingly, the first set of contacts 210a electrically engage pins 146 extending from openings 142 formed in upper portion 140b of prong receptacle 140. In addition, the second set of contacts 210b electrically engage pins 146 extending from opening 142 formed in lower portion 140a of prong receptacle 140.

Figure 12:
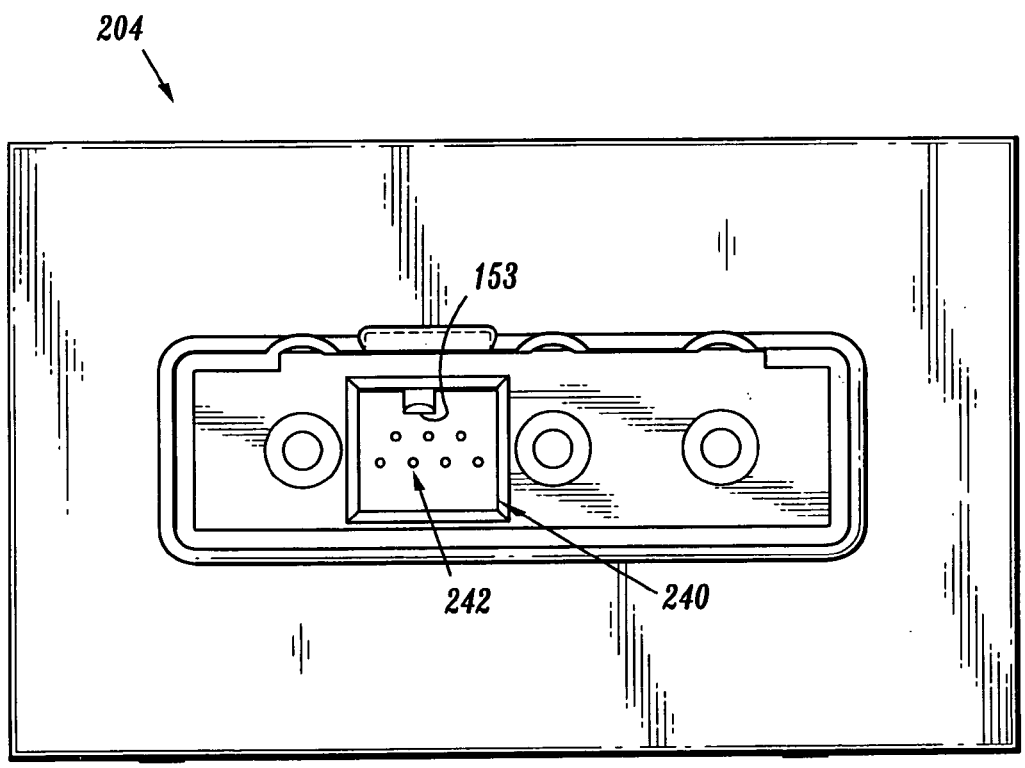
FIG. 12 is a front elevational view of a receptacle portion according to an alternate embodiment of the present disclosure.
Figure 13:
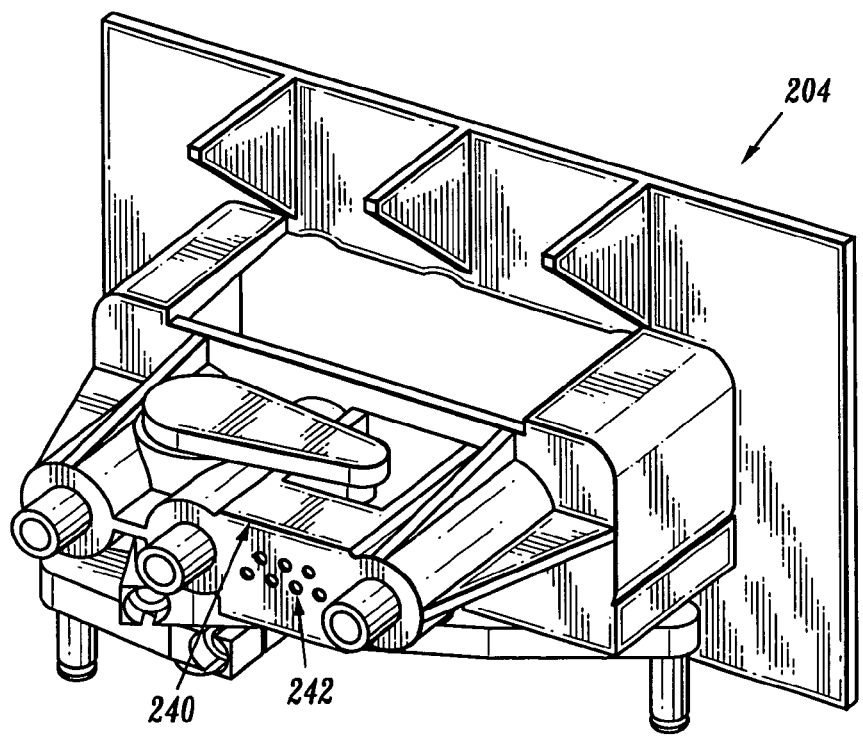
FIG. 13 is a rear perspective view of the receptacle portion of FIG. 12.

Turning now to FIGS. 12 and 13, a receptacle portion, in accordance with an alternate embodiment of the present disclosure, is designated generally as 204. Receptacle portion 204 is similar to receptacle portion 104 and will only be described in detail to the extent necessary to identify differences in construction and/or operation.

Receptacle portion 204 includes a prong receptacle 240 having a substantially rectilinear cross-sectional profile. Prong receptacle 240 is configured and dimensioned to receive prong 114 and/or prong 214 therein. Prong receptacle 240 includes a plurality of openings 242 formed in a rear wall 244 thereof. Preferably, two rows of openings 242 are formed, a first row including three openings and a second row including four openings. A pin 146 (not shown) can extend from each opening 242 for electrical engagement with contacts 210.

Figure 14:
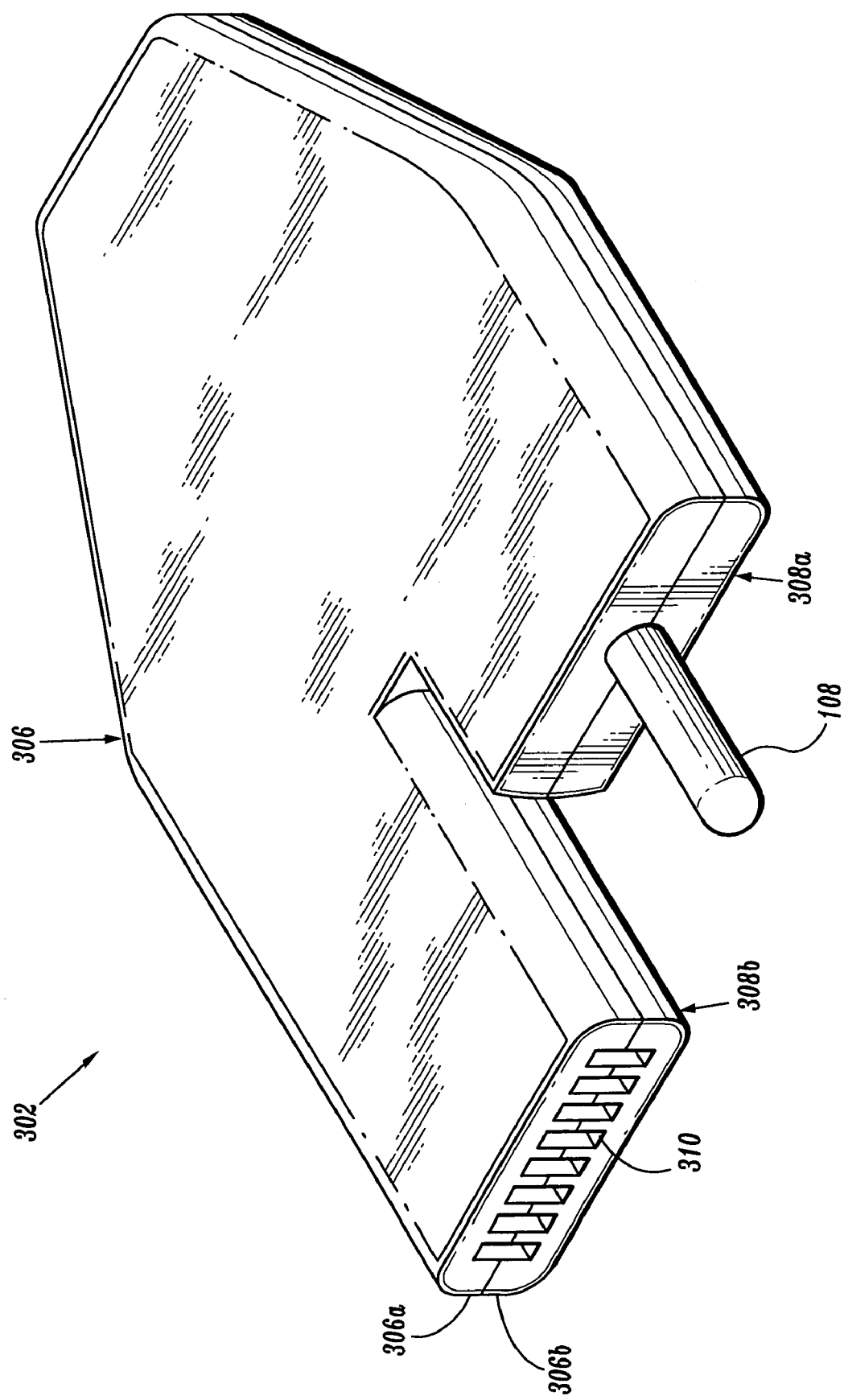
FIG. 14 is a perspective view of a plug portion in accordance with yet another embodiment of the present disclosure.

Turning now to FIG. 14, a plug portion, in accordance with yet another alternate embodiment of the present disclosure, is designated generally as 302. Plug portion 302 includes a housing 306 including a first half-section 306a and a second half-section 306b defining a plane therebetween. Housing 306 further includes a first side portion 308a and a second side portion 308b. Preferably, second side portion 308b has a length which is greater than a length of first side portion 308a.

As seen in FIG. 14, power pin 108 extends distally from first side portion 308a. Preferably, power pin 108 extends from first side portion 308a an amount sufficient such that a distal-most end of power pin 108 is substantially even with a distal-most surface of second side portion 308b.

Second side portion 308b includes a plurality of contacts 310 exposed along the distal-most surface thereof. In particular, second side portion 308b includes eight contacts 310 exposed along a distal-most surface thereof. Preferably, contacts 310 are in the same plane as power pin 108.

It is envisioned that electrosurgical generator 14 includes a receptacle portion (not shown) configured and dimensioned to receive and mate with plug portion 302.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

The invention claimed is:

1. A connector system for connecting an electrosurgical instrument to an electrosurgical generator, the connector system comprising:
   a plug portion connectable to the electrosurgical instrument, said plug portion including a plurality of pins which extend outwardly therefrom and an electrical prong which extends outwardly therefrom;
   a plug receptacle portion disposed within the generator, said plug receptacle portion defining a recess for receiving said plug portion therein, said plug receptacle portion including a corresponding plurality of pin receptacles for receiving said pins from said plug portion and said plug receptacle also including a prong receptacle for receiving said prong, said prong receptacle including a smart connection which is backward; and
   a tactile feedback mechanism for providing positive feedback to a user that the plug portion has been properly inserted into the plug receptacle portion, wherein the tactile feedback mechanism includes:
      a first post extending through and pivotally supported on the plug receptacle portion, wherein the first post is spring biased;
      a second post extending through and supported on the plug receptacle portion;
      a linkage member extending between the first post and the second post, the linkage member including a first arm extending radially from the first post and a second arm supported on and extending from the second post; and
      a camming pin extending through a distal end of the first arm, the camming pin including:
         a first portion slidably receivable in an elongate slot formed in the second arm;
         a second portion slidably receivable in an arcuate slot formed in the prong receptacle, the second portion extending an amount sufficient to engage a groove formed in a lower surface of the prong; and
         a spring positioned to bias the first portion to a distal-most position of the elongate slot.

2. A connector system for connecting an electrosurgical instrument to an electrosurgical generator, the connector system comprising:
   a plug portion and a plug receptacle portion disposed on said generator, said plug portion including a plurality of mechanical interfaces which selectively mate with a corresponding plurality of mechanical interfaces in said plug receptacle portion;

a tactile feedback mechanism for providing positive feedback to the user that the mechanical interfaces of said plug portion have been properly mated with said corresponding mechanical interfaces of said plug receptacle portion, said tactile feedback mechanism including:

a pair of first and second posts extending through and pivotally supported on the plug receptacle portion;

a linkage member extending between the first post and the second post, the linkage member including a first arm extending radially from the first post and a second arm supported on and extending from the second post; and a camming pin extending through a distal end of the first arm wherein upon insertion of the plug portion into the receptacle portion said camming pin rides along a slot disposed in said second arm to initially compress a spring which subsequently expands to drive the camming pin through the slot thus towing said prong portion into prong receptacle portion.

* * * * *